US012569155B2

(12) United States Patent
Cho et al.

(10) Patent No.: US 12,569,155 B2
(45) Date of Patent: Mar. 10, 2026

(54) IMPLANTABLE PRESSURE SENSING DEVICE FOR LONGITUDINAL INTRACRANIAL PRESSURE MONITORING

(71) Applicant: Wisconsin Alumni Research Foundation, Madison, WI (US)

(72) Inventors: Daniel Cho, Madison, WI (US); Jessica Blum, Middleton, WI (US); John Puccinelli, Cottage Grove, WI (US); James Trevathan, Arena, WI (US); Karina Buttram, Tempe, AZ (US); Caroline Craig, Verona, WI (US); Vivian Woo, Lakeville, MN (US); Joseph Ho, Greenfield, WI (US); Adrienne Simpson, Marshall, MN (US); Michael DelSignore, Madison, WI (US); Lucas Cates, Hamel, MN (US); Ipek Naz Kadioglu, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 316 days.

(21) Appl. No.: 18/498,331

(22) Filed: Oct. 31, 2023

(65) Prior Publication Data

US 2025/0134406 A1 May 1, 2025

(51) Int. Cl.
*A61B 5/03* (2006.01)
*A61B 5/00* (2006.01)

(52) U.S. Cl.
CPC ............ *A61B 5/031* (2013.01); *A61B 5/6868* (2013.01); *A61B 2560/04* (2013.01); *A61B 2562/0247* (2013.01)

(58) Field of Classification Search
CPC ......... A61B 5/03; A61B 5/031; A61B 5/6868; A61B 2560/04; A61B 2562/0247
See application file for complete search history.

(56) References Cited

U.S. PATENT DOCUMENTS

| | | | | |
|---|---|---|---|---|
| 4,172,449 A * | 10/1979 | LeRoy | A61B 5/03 600/561 |
| 4,385,636 A * | 5/1983 | Cosman | A61B 5/031 600/561 |
| 4,627,443 A * | 12/1986 | Chubbuck | A61B 5/031 600/561 |
| 2019/0328249 A1 * | 10/2019 | Lee | A61B 5/031 |
| 2020/0179664 A1 * | 6/2020 | Demetriou | A61B 5/031 |

* cited by examiner

*Primary Examiner* — Chu Chuan Liu
(74) *Attorney, Agent, or Firm* — Boyle Fredrickson, S.C.

(57) ABSTRACT

An intracranial pressure measurement device has a first plate abutting a patient's dura mater and displaced from a second plate abutting an endocranial surface of the patient's skull. The displacement of the first plate and second plate during elevated intracranial pressures are indicated visually on the device and visible through, e.g., X-ray imaging. This allows the intracranial pressure to be correlated to the mechanical displacement of the first plate from the second plate.

20 Claims, 4 Drawing Sheets

IMPLANTABLE PRESSURE SENSING DEVICE FOR LONGITUDINAL INTRACRANIAL PRESSURE MONITORING

BACKGROUND OF THE INVENTION

The present invention relates to devices for measuring intracranial pressure (ICP) and, in particular, to an ICP measurement device allowing for quantitative pressure measurement.

Craniosynostosis is a birth defect in which a baby's skull joins together prematurely before the baby's brain is fully formed. As the baby's brain grows and develops, the skull becomes misshapen as the spaces between the skull bones fill with flexible sutures. As the sutures turn to bone, the skull grows in an abnormal shape. When this happens, the brain may not have enough room to grow to normal size, thus there is a pressure build up inside the skull.

ICP is the pressure that builds up in the intracranial space due to an excess of cerebrospinal fluid (CSF) or swelling of the brain. It has been shown that prolonged increase in ICP can result in seizures, stroke, permanent brain tissue damage, and death.

Once craniosynostosis is diagnosed in a baby, a surgical procedure may be used to remove the prematurely fused sutures, relieve the elevated ICP and correct the craniosynostosis, allowing the brain to grow properly. This surgery is typically performed within the first year to year and a half of life. The baby is monitored regularly, for 15 to 20 years, to make sure that the brain and skull develop properly otherwise surgical intervention may be necessary.

Current monitoring for improper brain and skull development includes assessment of symptoms and ophthalmological and cognitive reporting. For example, dilated fundoscopic exams for papilledema, optical coherence tomography scans, and identification of symptoms such as vision impairments, vomiting, headaches, and the like can be used to help detect a problem. However, these methods have low sensitivities and specificities. If undetected, inhibited brain growth can cause developmental delays or cognitive disfunction, therefore timely intervention is desired.

SUMMARY OF THE INVENTION

Measurement of intracranial pressure (ICP) can be used to determine risk levels for head trauma, hydrocephalus, and craniosynostosis in patients. In one clinical application, elevated ICP is a highly accurate measurement for determining optimal timeline and modality of therapeutic intervention for craniosynostosis patients.

Current methods for determining ICP are highly invasive, requiring a pressure sensor to be implanted through a burr hole in the dura mater, and the patient must be admitted to the intensive care unit for 24-hour observation. The anesthesia may lower the ICP providing an inaccurate measurement of ICP and there is high risk of complications, such as infection. An accurate, non-invasive ICP pressure sensor is needed to directly monitor elevated ICP in children diagnosed with craniosynostosis during their developmental stages to minimize further complications.

The present invention is a minimally invasive, mechanical ICP sensing device that can be implanted during an initial craniosynostosis surgery that is performed to reconstruct and widen the skull of a child patient. The mechanical ICP sensing device is a small device allowing the device to be implanted outside the dura mater and underneath the endocranial surface of the child's skull. The device will detect compression of the device between the dura mater and the skull that correlates to an increase in ICP. The compression of the device can be monitored through medical imaging such as X-ray imaging.

To read the mechanical ICP sensing device, the design will incorporate radiopaque material that can be viewed through X-ray imaging. The ICP readings can detect dangerous ICP levels in the range of 15-20 mmHg indicating that intervention is necessary to relieve the pressure buildup in the skull. The mechanical ICP sensing device allows for ICP readings to be made more frequently and noninvasively over the lifespan of patient monitoring. The device acts as a pressure sensing device in the skull for 24 hours a day, and for over 15 to 20 years, during the duration of desired patient monitoring. The mechanical ICP sensing device does not need to be recalibrated. The mechanical ICP sensing device can remain in the patient's skull after monitoring is complete and for the patient's lifetime without adverse effect.

The present invention provides a pressure measurement device having a first plate displaced opposite a second plate abutting an endocranial surface of the skull. The displacement of the first plate and second plate is visually indicated on the device and visible through X-ray imaging. This allows the intracranial pressure to be correlated to the displacement of the first plate from the second plate.

In one embodiment, the present invention is a pressure measurement device for measuring intracranial pressure (ICP), the device comprising a first plate, the first plate positioned adjacent to an endocranial surface of the patient's skull. A second plate is displaced substantially parallel to the first plate, the second plate positioned adjacent to dura mater of the patient's skull. A displacement of the second plate from the first plate is indicated visually by movement of a mechanical marker. The mechanical marker is configured to be visible through medical imaging of the patient's skull.

It is thus a feature of at least one embodiment of the present invention to implant a pressure measurement device in the intracranial space during initial craniosynostosis surgery in a baby that further translates the mechanical movement of the device in response to pressure changes in the intracranial spaces into a visual indication of ICP.

The first plate and the second plate may be spring biased apart. The first plate and the second plate may be joined by at least one spring at least one corner of the first and second plate. The first plate and the second plate may be joined by two springs at opposite corners of the first and second plate. Alternatively, the first plate and the second plate may be joined by an elastomeric material.

It is thus a feature of at least one embodiment of the present invention to use a direct correlation between mechanical displacement of two plates between the dura mater and the skull and the ICP to provide an accurate measurement of the ICP.

The mechanical marker may be a sliding bar whereby displacement of the second plate from the first plate is directly correlated to a displacement of the sliding bar along an axis. Alternatively, the mechanical marker may be radiopaque markers coupled to the first plate and second plate whereby displacement of the radiopaque markers is directly correlated to ICP.

It is thus a feature of at least one embodiment of the present invention to allow the displacement of the two plates to be visualized by the positioning of a marker that is easy to see and whose change in position is directly correlated to the displacement of the two plates.

A push finger may be coupled to the second plate whereby the push finger is configured to press on the sliding bar when the second plate moves toward the first plate.

It is thus a feature of at least one embodiment of the present invention to provide a sliding indicator to visually indicate a marker position to the physician through X-ray imaging. The mechanical indicator does not require calibration and is less expensive or prone to malfunction than electrical indicators.

At least one roller may be rotatable perpendicular to the axis and configured to allow the sliding bar to slide along the axis. A spring may bias the sliding bar against movement along the axis.

It is thus a feature of at least one embodiment of the present invention to correlate the movement or position of the visible marker to ICP in the patient's skull using the relationship between spring forces and minimizing friction forces.

The mechanical marker may be radiopaque and visible through X-ray imaging.

It is thus a feature of at least one embodiment of the present invention to allow for inexpensive and widely available medical imaging techniques to be used to read the ICP.

At least one of the first plate and second plate may include a window that is radiolucent.

It is thus a feature of at least one embodiment of the present invention to provide ease in reading the marker position and which may be facilitated by line markings or other visual indicators or labels.

A displacement of the mechanical marker may be directly correlated to ICP.

It is thus a feature of at least one embodiment of the present invention to provide an ICP sensing device using mechanical components only and void of electrical components.

A method of measuring an intracranial pressure (ICP) inside a patient's skull comprises installing a first plate adjacent to an endocranial surface of the patient's skull; installing a second plate adjacent to dura mater of the patient's skull; imaging a position of a mechanical marker supported by the first plate and second plate and directly correlated to a displacement of the second plate from the first plate through medical imaging of the patient's skull, wherein the displacement of the second plate from the first plate is directly correlated to ICP; and determining the ICP inside the patient's skull indicated by the position of the mechanical marker.

The medical imaging may be X-ray imaging. The mechanical marker may be radiopaque. The mechanical marker may be visible through a radiolucent window.

The mechanical marker may be a sliding bar whereby displacement of the second plate from the first plate is directly correlated to a displacement of the sliding bar along an axis.

The second plate may support a push finger whereby push finger presses on the sliding bar when the second plate moves toward the first plate.

The first plate and the second plate may resist the pressure of the dura mater on the skull using a biasing spring positioned between the first plate and the second plate. The sliding bar may be biased against the push finger by a spring positioned between the sliding bar and a sidewall.

These particular objects and advantages may apply to only some embodiments falling within the claims and thus do not define the scope of the invention.

DETAILED DESCRIPTION OF THE PREFERRED EMBODIMENT

Figure 1:
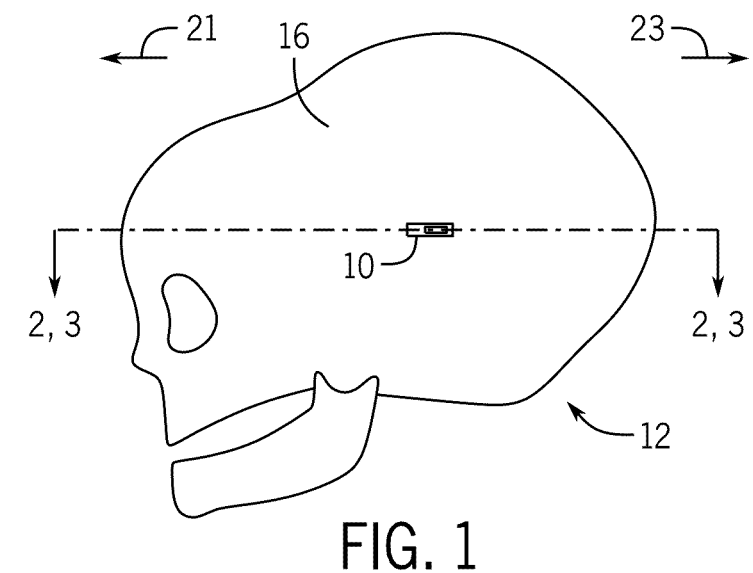
FIG. 1 is a fragmentary, perspective view of the pressure sensing device of the present invention as attached to the skull of a patient and visible through X-ray imaging.
Figure 2:
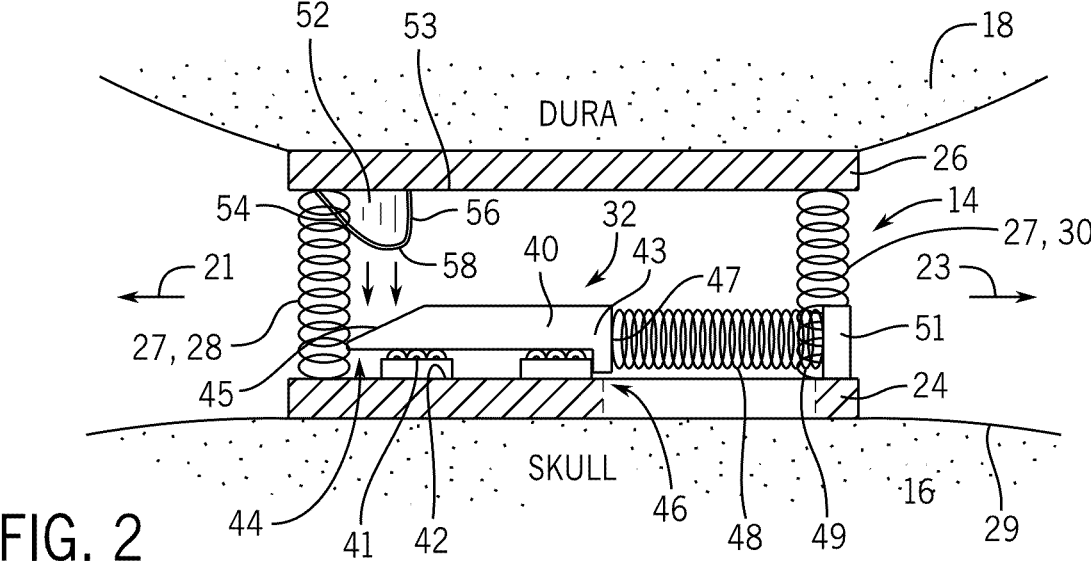
FIG. 2 is a top view of the pressure sensing device of FIG. 1 taken along line 2-2 in a neutral position with a cover removed showing a housing with opposing plates joined by compression springs and a forwardly extending finger compressing the biasing spring upon compression of the opposing plates.

Referring to FIGS. 1 and 2, a pressure sensing device 10 according to the present invention may attach, for example, to the endocranial surface of the skull of a patient 12 to support the pressure sensing device 10 in the intracranial space 14 between the skull 16 of the patient 12 and the dura mater 18 covering the brain of the patient 12. The pressure sensing device 10 is placed on the left lateral skull, as shown in FIG. 1, or the opposite right lateral skull, which is easier to see in X-ray imaging than the front or back of the skull 16. However, it is contemplated that the pressure sensing device 10 may be positioned anywhere on the skull 16 and which may be desired to detect ICP variations in different areas of the skull 16. The pressure sensing device 10 is worn by the patient 24-hours a day, seven days a week to allow for ICP in the skull 16 to be conveniently measured through X-ray imaging for 10-15 years following implantation.

The pressure sensing device 10 may be small enough (length and width) to be installed in the patient's intracranial space 14 and be thin enough (depth) so that it does not limit the flow of cerebrospinal fluid that would cause the brain to reshape. The pressure sensing device 10 may be approximately 1 cm long and 5 mm wide The depth of the pressure sensing device 10 in a neutral, non-compressed state may be no deeper than approximately 5 mm and may be approximately less than 5 mm or 1-5 mm in a partially or fully compressed state.

The pressure sensing device 10 is described herein with respect to an anterior direction 21 and posterior direction 23 of the patient's skull 16 but it is understood that the orientation of the pressure sensing device 10 and its components may be rotated, reversed or mirrored, for example, if placed on the other lateral side of the patient's skull 16 without affecting the general operation of the invention as understood by one having ordinary skill in the art.

Figure 3:
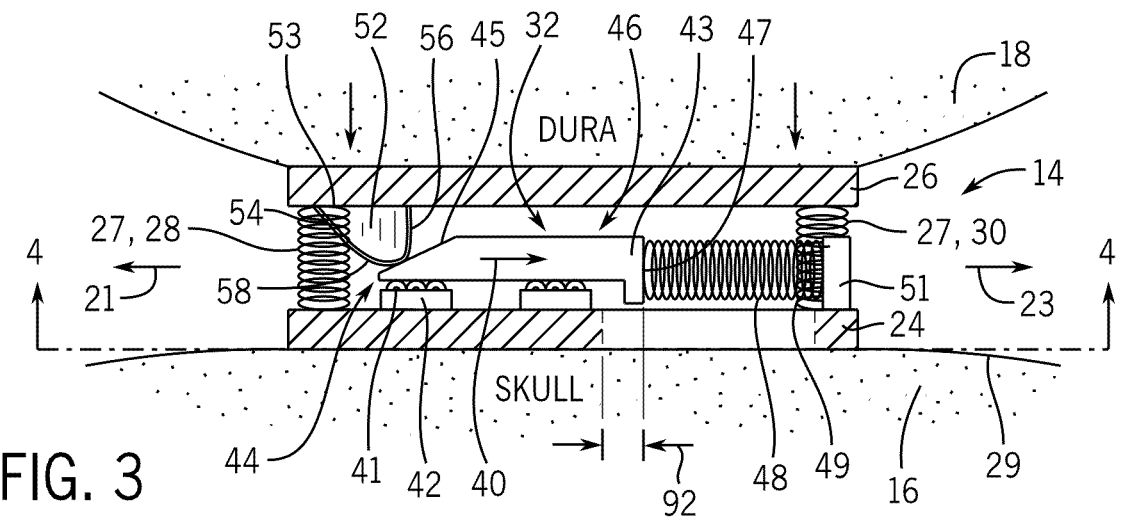
FIG. 3 is a top view of the pressure sensing device of FIGS. 1 and 2 taken along line 3-3 of FIG. 1 in a compressed position with a cover removed showing compression on the skull moving the plates toward each other and the finger pushing a slider to compress the biasing spring, where the slider and/or biasing spring can be imaged by X-ray imaging.

Referring now to FIGS. 2 and 3, the pressure sensing device 10 may include a first plate 24 and a second plate 26 that are rectangular parallel plates joined by a biasing member 27 that is a set of springs 28, 30 that bias the first and second plates 24, 26 away from each other. The first and second plates 24, 26 are joined by the set of springs 28, 30 at opposite corners of the first and second plates 24, 26, for example, the top anterior corner and the bottom posterior corner of the first and second plates 34, 26, respectively. The set of springs 28, 30 may include two springs but in alternative embodiments may include one spring or more than two springs preferably arranged at the corners of the first and second plates 24, 26 but may also be arranged along the edges or in the interior of the plates 24, 26. The springs 28, 30 may be made of spring steel. It is understood that the outer corners of the first and second plates 24, 26 may be rounded or smoothed to avoid lacerating the surrounding tissue.

As seen in FIG. 3, as the ICP increases in the intracranial space 14, the dura mater 18 around the brain will expand toward the skull 16 causing the rectangular plates 24, 26 to move toward each other. In one embodiment, the first plate 24 is installed on the inner, endocranial surface 29 of the skull 16, and the second plate 26 is positioned opposite and parallel to the first plate 24 adjacent to and against the dura mater 18. As the ICP increases, the dura mater 18 moves toward the skull 16 and the second plate 26 moves toward the first plate 24. The movement of the second plate 26 toward the first plate 24 causes the springs 28, 30 joining the plates 24, 26 to compress. The movement of the plates 24, 26 toward each other and compression of the springs 28, 30 causes an imaging marker 32 to provide a visible indication of the ICP that can be seen by a physician through X-ray imaging. The displacement of the plates 24, 26 may be correlated to ICP prior to implantation of the pressure sensing device 10 in a manner which allows the physician to determine the ICP with good accuracy as discussed below with respect to FIGS. 7 through 9.

The imaging marker 32 of the pressure sensing device 10, in one embodiment seen in FIGS. 2 and 3, may include a sliding bar 40 supported on the first plate 24 by sliding supports such as wheels or rollers 41 which allow the sliding bar 40 to move freely, linearly in a posterior direction minimizing the effects of friction. In one embodiment, the rollers 41 are a set of three cylinders set in a box or well 42 allowing the top of the cylinders to rotate freely about axes perpendicular to the anterior/posterior directions 21, 23 and contact the bottom of the sliding bar 40 in a sliding manner. In an alternative embodiment, the sliding supports may be rounded brackets (not shown) allowing the sliding bar 40 to slide along the top of the rounded brackets. The brackets may also constrain the movement of the sliding bar 40 along a linear axis.

The sliding bar 40 is generally rectangular and extends along the first plate 24 with an anterior end 44 that is pushed posteriorly when the plates 24, 26 are compressed and a posterior end 46 that presses against a biasing spring 48 as it is pushed posteriorly. The anterior end 44 of the sliding bar 40 includes an angled surface 45 that slopes rearwardly toward the second plate 26 from the anterior end 44 to the posterior end 46. The posterior end 46 of the sliding bar 40 supports a posterior vertical wall 43 that may extend forwardly towards the first plate 24 providing a broadened surface to support a first end 47 of the biasing spring 48 biasing the sliding bar 40 in the anterior direction 21. An opposite second end 49 of the biasing spring 48 is attached to an outer support wall 51, spaced from and parallel to the posterior vertical wall 43, and located at a posterior edge of the first plate 24. The sliding bar 40 may be prevented from sliding off the first plate 24 by the outer support wall 51 on the posterior end 46 and the posterior vertical wall 43 hitting the rollers 41 on the anterior end 44.

The second plate 50 supports a push finger 52 that extends forwardly from the inner surface 53 of the second plate 50 toward the first plate 24. The push finger 52 has a triangular form with an angled anterior surface 54 and a flat posterior surface 56 joining at a tip 58 that contacts the angled surface 45 of the anterior end 44 of the sliding bar 40 in a partial or fully compressed state. When the second plate 50 moves toward the first plate 24 during compression, the push finger 52 moves forwardly with the forward motion of the second plate 50. As the tip 58 of the push finger 52 presses on the angled surface 45 of the anterior end 44 of the sliding bar 40, the sliding bar 40 is pushed in the posterior direction 23 and the tip 58 slides along the angled surface 45 as the sliding bar 40 advances posteriorly. The movement of the sliding bar 40 in the posterior direction 23 presses against the first end 47 of the biasing spring 48 compressing the biasing spring 48 against the outer support wall 51. The movement of the sliding bar 40 and/or change in length of the biasing spring 48 act as the imaging marker 32 that can be seen through medical imaging as further discussed below.

Figures 4, 5, 6:
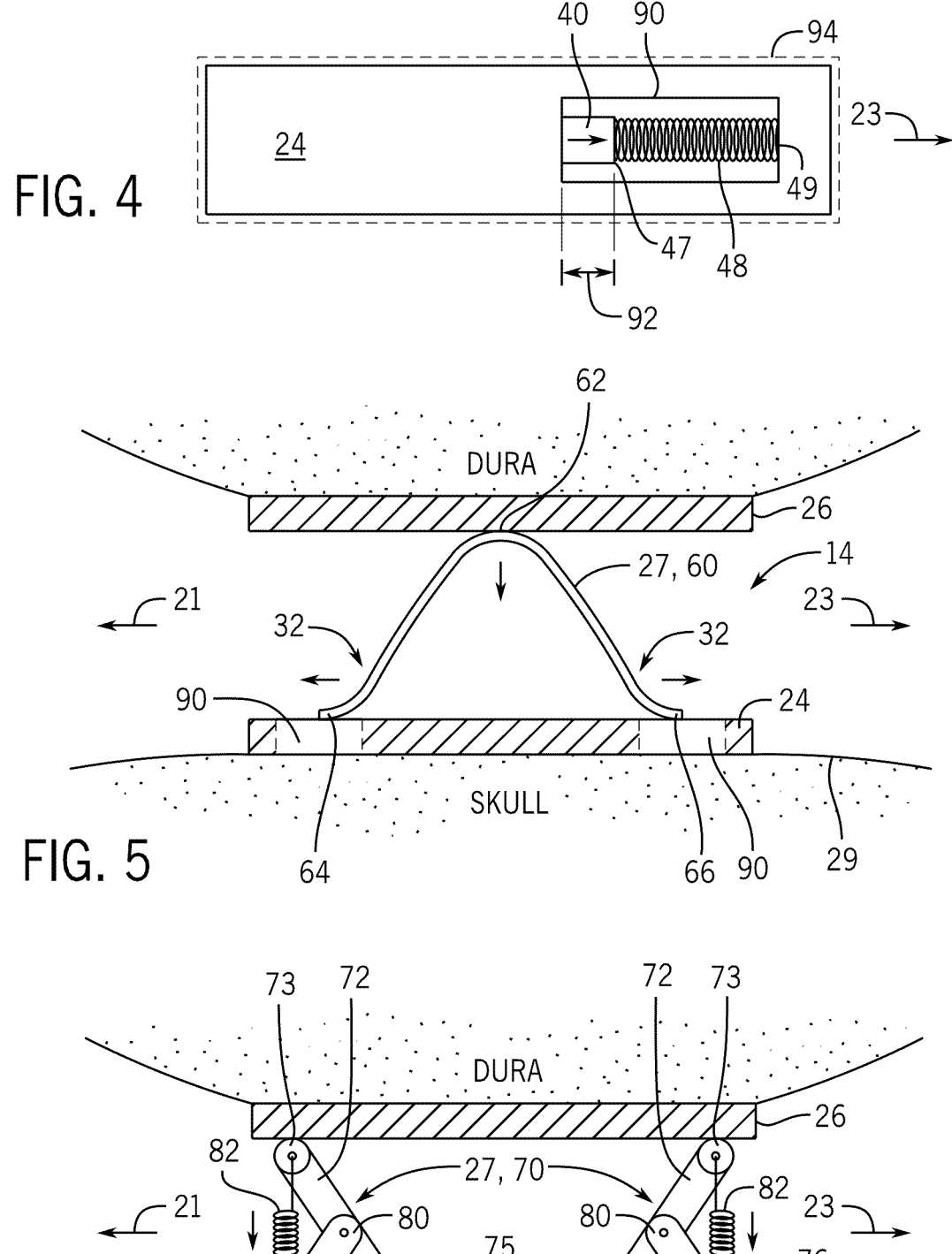
FIG. 4 is a front, elevational view of the pressure sensing device of FIGS. 1-3 taken along line 4-4 of FIG. 3 with a front plate of the device showing a radiolucent window that allows the slider and/or spring to be imaged by X-ray imaging.
FIG. 5 is a top view of an alternative embodiment of the pressure sensing device with a cover removed showing a housing with opposing plates joined by a flexible spring clip that bends to expand and slide the outer ends of the clip with compression of the opposing plates, where the outer ends of the clip can be imaged by X-ray imaging.
FIG. 6 is a top view of an alternative embodiment of the pressure sensing device with a cover removed showing a housing with opposing plates joined by a pair of rolling linkages that bend at a hinge to slide a roller of the linkages with compression of the opposing plates, where the roller can be imaged by X-ray imaging.

Referring briefly to FIG. 5, in an alternative embodiment, the biasing member 27 and imaging marker 32 as described above with respect to FIGS. 2 and 3 may be replaced by a flexible spring clip 60 formed by a metal bar shaped in a U-shape and defined by a middle hill 62 attached to one of the first and second plates 24, 26 and opposed ends 64, 66 of the U-shaped spring clip 60 attached to the other of the first and second plates 24, 26. In one embodiment, the middle hill 62 of the spring clip 60 is fixedly attached to the second plate 26 and the opposed ends 64, 66 of the spring clip 60 are movably attached to the first plate 24 in an outwardly sliding manner. The opposed ends 64, 66 of the U-shaped spring clip 60 may be retained to the second plate 26, for example, with clips or brackets, but allowed to slide outwardly, in anterior 21 and posterior 23 directions, respectively, when the clip 60 is compressed.

The movement of the first and second plates 24, 26 as described above when the ICP increases causes the spring clip 60 joining the plates 24, 26 to compress causing the ends 64 of the spring clip 60 to move outwardly in anterior 21 and posterior 23 directions, respectively. The outward movement of the ends 64 of the spring clip 60 provide a visual indication/imaging marker 32 that correlates the movement of the first and second plates 24, 26 with the patient's ICP that can be seen by a physician through X-ray imaging. In one embodiment, the ends 64 of the spring clip 60 may support radiopaque markers which act as the imaging marker 32.

Referring briefly to FIG. 6, in another alternative embodiment, the biasing member 27 and imaging marker 32 as described with respect to FIGS. 2 and 3 may be replaced by a pair of rolling linkages 70, generally known as a Scott Russell mechanism, where a first linkage arm 72 is attached to one of the first and second plates 24, 26 at a hinge joint 73 on a first end and a sliding mechanism such as a roller 74 on a second end, where the roller 74 contacts the other of the first and second plates 24, 26 and is freely moveable along the plate. A second linkage arm 76 is attached to the other of the first and second plates 24, 26 at a hinge joint 78 at a first end and attached to the middle section of the first linkage arm 72 at a hinge joint 80 on a second end. A spring 82 may attach the hinge joint 73 of the first linkage arm 72 and the hinge joint 78 of the second linkage arm 76 creating a tension that biases the first and second plates 24, 26 apart from each other. In one embodiment, the joint 73 of the linkage arm 72 is attached to the second plate 26 and the roller 74 contacts the first plate 24. The joint 78 of the second linkage arm 76 is attached to the first plate 24.

The movement of the first and second plates 24, 26 as described above when the ICP increases causes the spring 82 to compress and the hinge joint 73 of the first linkage arm 72 and the hinge joint 78 of the second linkage arm 76 to come closer together. This causes the roller 74 to slide or translate along the first plate 24. The sliding movement of the roller 74 of the rolling linkage 70 provides the visual indication/imaging marker 32 that correlates the movement of the first and second plates 24, 26 with the patient's ICP that can be seen by a physician through X-ray imaging. In one embodiment, the roller 74 of each linkage 70 may be attached to each other by a rubber bellow 75, and radiopaque markers on the respective rollers 74 may indicate a distance between the rollers 74 and act as the imaging marker 32.

Referring again to FIGS. 2, 3 and now FIG. 4, the imaging marker 32, which may be the sliding bar 40 as seen in FIGS. 2 and 3 (or alternatively, and in a similar manner, the imaging markers 32 of the embodiments shown in FIGS. 4 and 5), that can be viewed through a radiolucent window 90 in the first plate 24 allowing the sliding bar 40 and/or biasing spring 48, which are made of a radiopaque material, to be easily visualized with X-ray imaging along a plane substantially perpendicular to the direction of device compression. The radiolucent window 90 may be positioned adjacent the biasing spring 48 such that the first end 47 of the biasing spring 48 and the second end 49 of the biasing spring 48 are seen when the biasing spring 48 is in a neutral position. Therefore, the radiolucent window 90 may extend from the posterior vertical wall 43 to the outer support wall 51 when the biasing spring 48 is in the neutral position. The radiolucent window 90 can act as a ruler or gauge to help the physician quickly visualize movement/position of the sliding bar 40 and/or biasing spring 48. In this respect, the radiolucent window 90 may be lined with line markers or other visual indicators or labels to allow the physician to correlate movement/position of the sliding bar 40 and/or biasing spring 48 with the patient's ICP level.

In one embodiment, the radiolucent window 90 may be approximately 25 mm tall and 37 mm wide. The radiolucent window 90 may be made of radiolucent materials, for example, plastics or radiolucent composites such as plastic matrices or fiber reinforced plastics such as glass fibers and carbon fibers. The sliding bar 40 and biasing spring 48 may be made of radiopaque materials, for example, metals such as aluminum, stainless steel and titanium. The first plate 24 may also be radiopaque, besides the radiolucent window 90, while the second plate 26 may be radiolucent to help visualize the radiopaque sliding bar 40 and biasing spring 48.

As seen in FIG. 4, when the second plate 26 moves toward the first plate 24 to different degrees of compression as the ICP increases, the push finger 52 will press on the angled surface 45 of the anterior end 44 of the sliding bar 40 to advance the sliding bar 40 in the posterior direction 23 a displacement distance 92, and in view of the radiolucent window 90. It is expected that the level of ICP will be correlated with the amount of advancement or displacement 92 of the sliding bar 40, which can be viewed directly through the radio translucent window 90 via X-ray imaging.

For example, movement of the sliding bar 40 a displacement distance 92 of about 0.5 mm to 1.5 mm and extending within the view of the translucent window 90, may indicate elevated ICP in the range of 15-20 mmHg or more. When an elevated ICP is indicated through X-ray imaging of the patient's skull and viewing the pressure sensing device 10, surgical interventional can be implemented to alleviate the elevated pressure.

It is understood that alternative embodiments of the invention may include, for example, multiple translucent windows 90 arranged along the advancement or displacement direction of the sliding bar 40 in the posterior direction to indicate different levels of ICP. For example, as the sliding bar 40 extends a greater displacement distance 92, the sliding bar 40 may extend across additional translucent windows 90 (e.g., a first window indicating 0-5 mmHg, a second window indicating 5-10 mmHg, a third window indicating 10-15 mmHg) thus indicating incrementally increasing ICP levels as compression of the plates 24, 26 increases.

Figure 7:
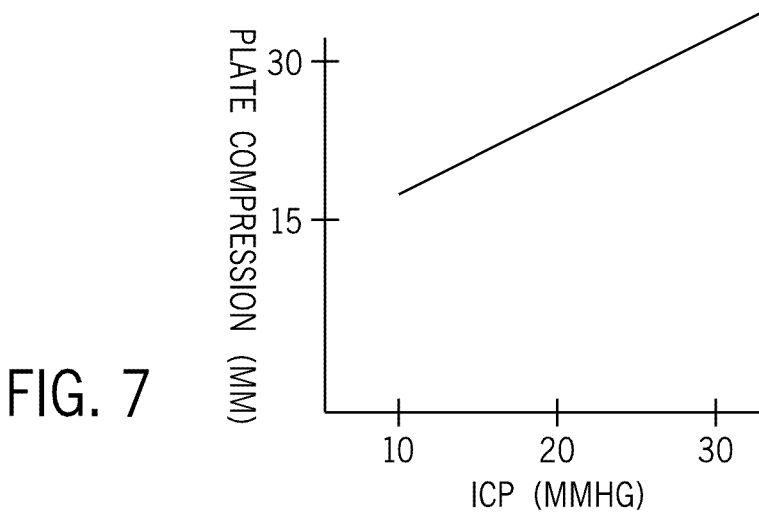
FIG. 7 is a graph showing a linear correlation between ICP and the compression of the plates of the pressure sensing device of FIGS. 1-3.

Referring to FIG. 7, the ICP (measured in mmHg) in the intracranial space 14 is directly correlated to the compression of the plates 24, 26 (measured in mm). Therefore, the mechanical compression of the plates 24, 26 is shown to be a good indicator of the ICP in the intracranial space 14. It is understood that the springs 28, 30 may have a desired stiffness or spring constant to correlate the compression of the plates 24, 26 with ICP.

Figure 8:
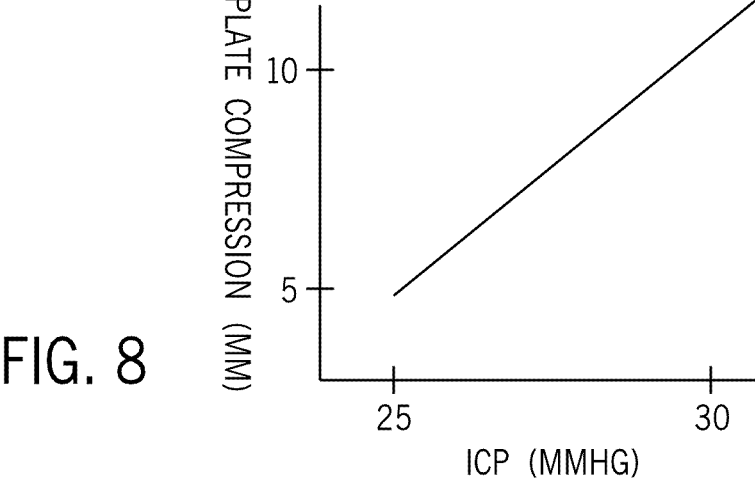
FIG. 8 is a graph showing a linear correlation between the compression of the plates and the advancement of the slider of the pressure sensing device of FIGS. 1-3.

Referring to FIG. 8, the compression of the plates 24, 26 (measured in mm) is directly correlated to the movement of the sliding bar 40 in the posterior direction 23 (measured in mm). It is understood that the springs 28, 30 and biasing spring 48 may have a desired stiffness or spring constant to correlate compression of the plates 24, 26 with the movement of the sliding bar 40. Therefore, the mechanical movement of the sliding bar 40 is shown to be a good indicator of the compression of the plates 24, 26.

Figure 9:
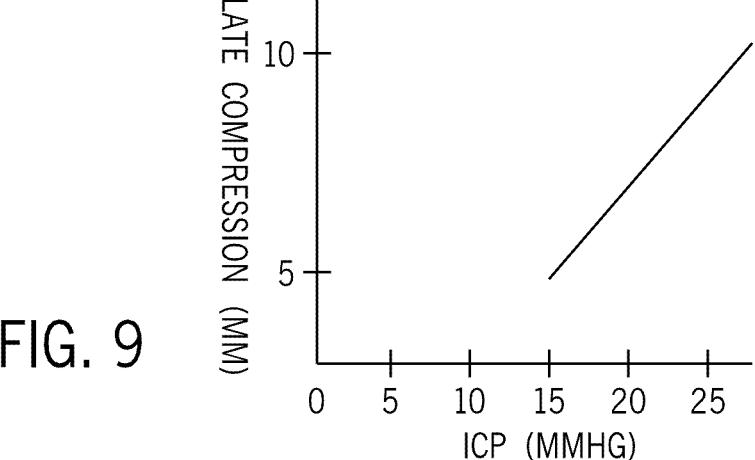
FIG. 9 is a graph showing the linear correlation between ICP and the advancement of the slider of the pressure sensing device of FIGS. 1-3.

Referring to FIG. 9, the ICP (measured in mmHg) in the intracranial space 14 is directly correlated to the movement of the sliding bar 40 in the posterior direction 23 (measured in mm). Therefore, the mechanical movement of the sliding bar 40 is shown to be a good indicator of the ICP in the intracranial space 14. It is understood that the biasing spring 48 may have a desired stiffness or spring constant to correlate the movement of the sliding bar 40 with ICP. As seen, an elevated ICP, for example, over 15 mmHg or over 20 mmHg, may be indicated by sliding bar 40 movement that is about 1 mm or more.

Referring again to FIG. 4, the pressure sensing device 10 may be enclosed by a cover 94 to protect the moving elements of the pressure sensing device 10 from the surrounding tissue and vice versa. The cover 94 may be at least partially radiolucent, for example, made of plastics or radiolucent composites such as plastic matrices or fiber reinforced plastics such as glass fibers and carbon fibers. Further, the cover 94 may be a nonbiodegradable, medical grade, FDA approved, and biocompatible material, thus allowing the pressure sensing device 10 to be implanted within the patient long term, for example, for at least 10 to 15 years, for monitoring, and in some instances may remain in the patient for the patient's lifespan without adverse effect. The cover 94 may seal the inner components of the pressure sensing device 10 thus preventing contamination. In one embodiment, the cover 94 may be medical grade silicone. The cover 94 may be attached to the patient's skull 16 using sutures or screws.

Figure 10:
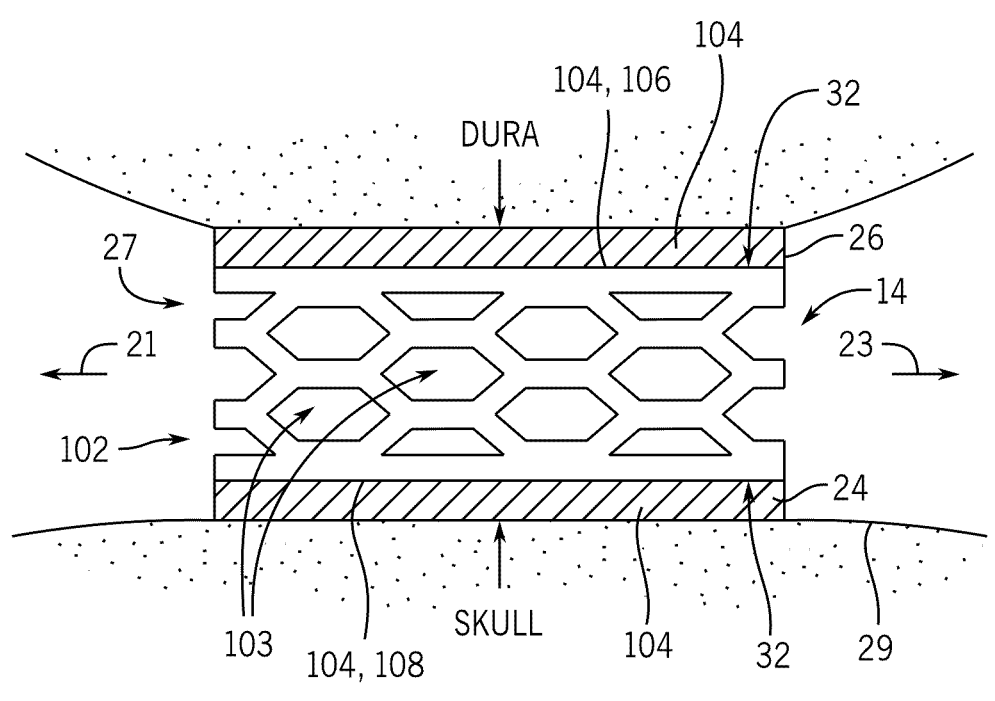
FIG. 10 is a top view of an alternative embodiment of the pressure sensing device with a cover removed showing a housing with opposing plates joined by an elastomer material with compression of the opposing plates compressing the elastomer material, where radiopaque markers coupled to the elastomer material can be imaged by X-ray imaging.

Referring to FIG. 10, in an alternative embodiment, the biasing member 27 and imaging marker 32 as described with respect to FIGS. 2 and 3 may be replaced by a rectangular block 102 of compressible material positioned between and attached to the first and second plates 24, 26, as shown in FIG. 10, or in certain embodiments, the first and second plates 24, 26 are omitted and the inner and outer walls 106, 108 of the rectangular block 102 may serve as the first and second plates 24, 26.

The compressible material may be an elastomer that can compress and deform but resume its normal shape after contraction. The compressible material may have an elastic modulus of 5 kPa-25 kPa and less than 25 kPa and less than 15 kPa and about 13.3 kPa. The compressible material desirably can provide a displacement of at least 2 mm and at least 3 mm and at least 4 mm and at least 5 mm when 5-40 mmHg of pressure is applied and when 5-20 mmHg of pressure is applied and when less than 40 mmHg is applied and as low as 5 mmHg is applied and when as low as 10 mmHg is applied.

The compressible material may be a bioinert (with minimal immune response) and biocompatible material (with minimal thrombogenicity) or alternatively, a material that is encapsulated in a bioinert and biocompatible covering. Desirably, the compressible material is non-biodegradable for at least ten years and can withstand a pH of 7.4±1.0. Desirably, the compressible material may maintain its elastic modulus and other physical and mechanical properties for at least 5 years and at least 10 years.

In certain embodiments, the compressible material may be a uniform polydimethylsiloxane (PDMS), hydrogel, and the like, coated with a thin layer of medical grade silicone or silicone rubber for biocompatibility. In certain embodiments, the outer surface of the rectangular block 102 may receive a surface treatment of silicone coating. The silicone coating may be micropatterned with a textured surface on a microscopic scale to increase biocompatibility and bioinertness. The silicone coating may assist with medication infusion (e.g., anticoagulants and/or antibiotics).

In certain embodiments, the rectangular block 102 of compressible material may be further enclosed by a biocompatible cover 94 as described above to protect the rectangular block 102 from the surrounding tissue. The biocompatible cover 94 may be at least partially radiolucent.

The rectangular block 102 may be formed as a solid bulk structure or lattice structure with spaces 103 that are rhombus, hexagonal, oblique, square, rectangular, and the like. In one embodiment, the lattice structure consists of six columns and two rows of hexagons spaces 103. In an alternative embodiment, and as shown in FIG. 10, the lattice consists of six columns and four rows of rhombi spaces 103. The rectangular block 102 of compressible material may be approximately 5 mm by 5 mm by 10 mm and may have a maximum height (in the direction of compression) of 5 mm. The lattice wall thickness may be about 0.125 mm.

The rectangular block 102 of compressible material may be flanked by imaging markers 32 which in one embodiment may be radiopaque plates 104 consisting of sheets or layers of radiopaque material, e.g., medical grade titanium alloy or titanium foil sheets, covering or lining exposed surfaces of the inner and outer walls 106, 108 of the rectangular block 102, as shown in FIG. 10, or alternatively, inner or outer surfaces of the separate first and second plates 24, 26. It is understood that if the inner and outer walls 106, 108 of the rectangular block 102 serve as the first and second plates 24, 26, the radiopaque plates 104 will cover or line the exposed surfaces of the inner and outer walls 106, 108 of the rectangular block 102.

In an alternative embodiment, the imaging markers 32 may be radiopaque markers of discrete points, rather than radiopaque plates, attached to the rectangular block 102 or the first and second plates 24, 26 flanking the rectangular block 102, and providing reference points. It is understood that the radiopaque markers may be plates, wires or particles which are visible through x-ray imaging.

As described above, as an intracranial pressure is increased and pressure is applied to the first and second plates 24, 26 and/or inner and outer walls 106, 108 of the rectangular block 102, the rectangular block 102 is deformed to compress the inner and outer walls 106, 108 of the rectangular block 102. The compression deformation across the rectangular block 102 of compressible material may be substantially uniform to provide a uniform displacement of the radiopaque plates 104.

The distance between the radiopaque plates 104 is directly correlated to ICP to provide a visual indication/imaging marker 32 of ICP as described above with respect to FIGS. 7 to 9 and visible through X-ray imaging. The pressure sensing device 10 is imaged along a plane that is substantially parallel to the direction of device compression permitting the distance between the radiopaque plates 104 to be visible. Therefore, compression of the rectangular block 102 of compressible material provides an alternative mechanical ICP sensing device.

It is understood that other medical brain imaging modalities such as computed tomography (CT) scan, magnetic resonance imaging (MRI), functional MRI, positron emission topography (PET), and the like may also be used in a similar manner as X-ray imaging in order to detect or see mechanical changes to the pressure sensing device 10.

In alternative embodiments, the pressure sensing device 10 may include a piezoresistive, microelectromechanical pressure sensor and a signal transmitter. An external device may consist of a radio frequency transmitter, signal receiver, and output reading display. When the external device is brought near the implanted pressure sensor, the radio frequency may trigger the implanted device 10 to power on, obtain a pressure reading based on, e.g., the deflection of resistors of the pressure sensor, and transmit an output signal via the signal transmitter back to the external device. The external device may convert the voltage output signal, e.g., using a Wheatstone Bridge, to a pressure sensor reading based on ADC conversion and display the pressure reading on an external display or screen.

It is understood that the electronic device may be used in combination with the mechanical systems described above.

It is understood that aspects of the mechanical systems described above may be combined and interchanged as well.

It is understood that the present invention may have other clinical applications besides craniosynostosis where measurement of ICP may be used to determine risk levels for a patient such as after head trauma or for patients with brain tumors, meningitis, hydrocephalus and the like.

Certain terminology is used herein for purposes of reference only, and thus is not intended to be limiting. For example, terms such as "upper", "lower", "above", and "below" refer to directions in the drawings to which reference is made. Terms such as "front", "back", "rear", "bottom" and "side", describe the orientation of portions of the component within a consistent but arbitrary frame of reference which is made clear by reference to the text and the associated drawings describing the component under discussion. Such terminology may include the words specifically mentioned above, derivatives thereof, and words of similar import. Similarly, the terms "first", "second" and other such numerical terms referring to structures do not imply a sequence or order unless clearly indicated by the context.

When introducing elements or features of the present disclosure and the exemplary embodiments, the articles "a", "an", "the" and "said" are intended to mean that there are one or more of such elements or features. The terms "comprising", "including" and "having" are intended to be inclusive and mean that there may be additional elements or features other than those specifically noted. It is further to be understood that the method steps, processes, and operations described herein are not to be construed as necessarily requiring their performance in the particular order discussed or illustrated, unless specifically identified as an order of performance. It is also to be understood that additional or alternative steps may be employed.

It is specifically intended that the present invention not be limited to the embodiments and illustrations contained herein and the claims should be understood to include modified forms of those embodiments including portions of the embodiments and combinations of elements of different embodiments as come within the scope of the following claims. All of the publications described herein, including patents and non-patent publications, are hereby incorporated herein by reference in their entireties.

To aid the Patent Office and any readers of any patent issued on this application in interpreting the claims appended hereto, applicants wish to note that they do not intend any of the appended claims or claim elements to invoke 35 U.S.C. 112(f) unless the words "means for" or "step for" are explicitly used in the particular claim.

What we claim is:

1. A pressure measurement device for measuring intracranial pressure (ICP) inside a patient's skull, the pressure measurement device comprising:
   a first plate, the first plate positionable adjacent to an endocranial surface of the patient's skull; and
   a second plate displaced substantially parallel to the first plate, the second plate positionable adjacent to dura mater of the patient's skull;
   wherein a displacement of the second plate from the first plate is indicated visually by movement of a mechanical marker, wherein the mechanical marker is configured to be visible through medical imaging of the patient's skull.

2. The pressure measurement device of claim 1 wherein the first plate and the second plate are biased apart.

3. The pressure measurement device of claim 2 wherein the first plate and the second plate are joined by an elastomeric material.

4. The pressure measurement device of claim 2 wherein the first plate and the second plate are joined by at least one spring.

5. The pressure measurement device of claim 1 wherein the mechanical marker comprises radiopaque markers coupleable to the first plate and second plate whereby a displacement of the radiopaque markers are directly correlated to ICP.

6. The pressure measurement device of claim 1 wherein the mechanical marker is a sliding bar sliding transverse to the displacement and a push finger coupled to the second plate whereby the push finger is configured to press on the sliding bar when the second plate moves toward the first plate.

7. The pressure measurement device of claim 6 further comprising at least one roller rotatable perpendicular to the axis and configured to allow the sliding bar to slide along the axis.

8. The pressure measurement device of claim 7 wherein the mechanical marker further comprises a spring biasing the sliding bar against movement along the axis.

9. The pressure measurement device of claim 1 wherein the mechanical marker is radiopaque and visible through X-ray imaging.

10. The pressure measurement device of claim 1 wherein at least one of the first plate and second plate includes a window that is radiolucent.

11. The pressure measurement device of claim 1 wherein a displacement of the mechanical marker is directly correlated to ICP.

12. A method of measuring an intracranial pressure (ICP) inside a patient's skull comprising:
   installing a first plate adjacent to an endocranial surface of the patient's skull;
   installing a second plate adjacent to dura mater of the patient's skull;
   imaging a position of a mechanical marker supported by the first plate and second plate and directly correlated to a displacement of the second plate from the first plate through medical imaging of the patient's skull, wherein the displacement of the second plate from the first plate is directly correlated to ICP; and
   determining the ICP inside the patient's skull indicated by the position of the mechanical marker.

13. The method of claim 12 wherein the medical imaging is X-ray imaging.

14. The method of claim 13 wherein the mechanical marker is radiopaque.

15. The method of claim 14 wherein the mechanical marker is a pair of radiopaque markers coupled to the first plate and second plate.

16. The method of claim 12 wherein a displacement of the radiopaque markers is directly correlated to ICP.

17. The method of claim 12 wherein the mechanical marker is a sliding bar sliding transverse to a displacement of the second plate from the first plate, and a sliding displacement of the sliding bar is directly correlated to ICP.

18. The method of claim 12 wherein the first plate and the second plate resist the pressure of the dura mater on the skull via a biasing element positioned between the first plate and the second plate.

19. The method of claim 18 wherein the biasing element is an elastomer positioned between the first plate and the second plate.

20. The method of claim 18 wherein the biasing element is a spring positioned between the first plate and the second plate.

\* \* \* \* \*